United States Patent [19]

Ferrari

[11] Patent Number: 4,911,169

[45] Date of Patent: Mar. 27, 1990

[54] BIOMEDICAL ELECTRODE WITH LIMB BAND

[76] Inventor: Robert K. Ferrari, 100 S. 13th St., P.O. Box 578, Herrin, Ill. 62948

[21] Appl. No.: 322,357

[22] Filed: Mar. 13, 1989

[51] Int. Cl.$^4$ ............................................. A61B 5/04
[52] U.S. Cl. ..................................... 128/641; 128/644
[58] Field of Search ............................. 128/639–641, 128/644, 798, 802, 803

[56] References Cited

U.S. PATENT DOCUMENTS 4,082,086  4/1978  Page et al. ........................... 128/640
4,088,133  5/1978  Twentler .............................. 128/644

FOREIGN PATENT DOCUMENTS 1003135  4/1977  Canada ................................ 128/644

OTHER PUBLICATIONS

Albisser et al., "Atraumatic ", JAAMI, vol. 5, No. 2, Mar.-Apr. 1971, pp. 73–76.
Jul.-Aug., 1987 Issue of Perinatology-Neonatology, p. 18.

Primary Examiner—Lee S. Cohen
Attorney, Agent, or Firm—Vernon J. Pillote

[57] ABSTRACT

A biomedical electrode with limb band for use on a limb of a patient comprising a composite electrode pad having an electrically conductive member with means for connection to an external sensing and monitoring apparatus, and a layer of electrically conductive solid gel adhesive contacting the conductive member and providing a skin contacting adhesive surface for attaching the electrode pad to the skin of a patient. A composite limb band includes an outer band formed of non-woven spunlaced polyester fibers and an inner band formed of non-woven spunbonded polyester filaments adhesively secured to an intermediate portion of the outer bank along the inner side thereof. A first end portion of the outer band is adhesively attached to the outer face of the composite electrode pad. The composite limb band has a length to encircle the limb of a patient, and a pressure sensitive adhesive is provided on the inner face of a second end portion of the outer band for adhesively attaching the second end portion onto the outer side of the composite band.

12 Claims, 2 Drawing Sheets

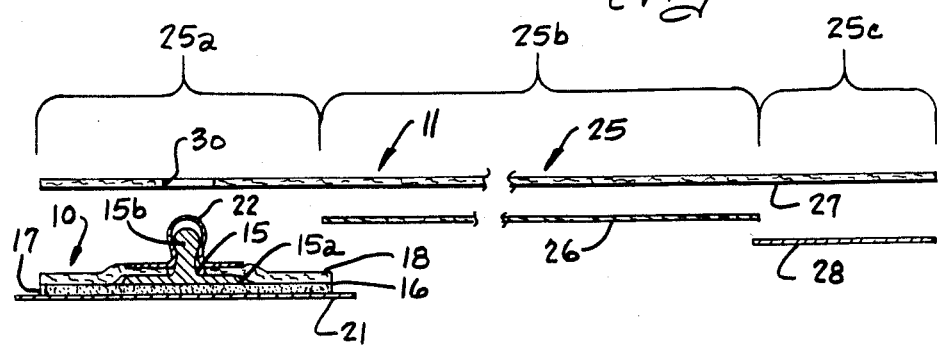
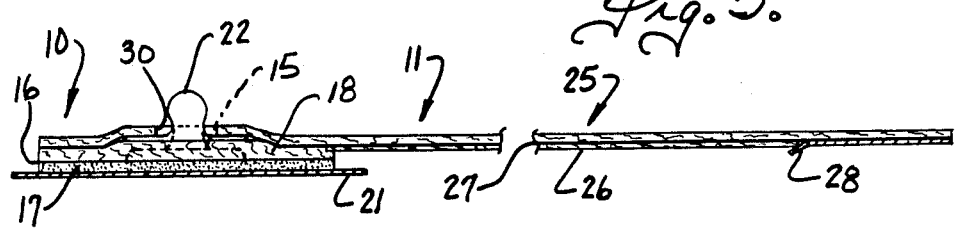
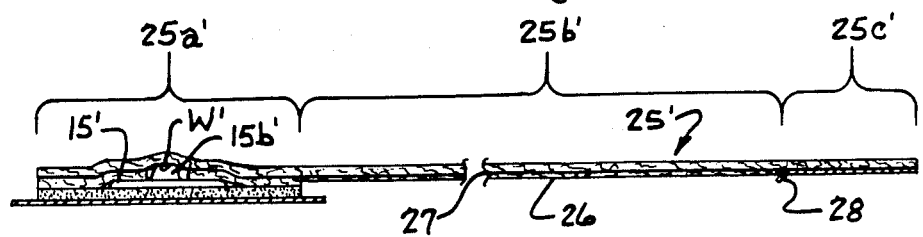

BIOMEDICAL ELECTRODE WITH LIMB BAND

BACKGROUND OF THE INVENTION

The present invention relates to biomedical electrodes and particularly to a biomedical electrode for use on a limb of an infant.

One form of limb band electrode heretofore made used a strip of vinyl plastic coated with a conductive layer along one side and a conductive gel laminated to the conductive layer along a length of the band such that the band could adhere around substantially the entire periphery of the limb of the infant. Another prior form of limb band electrode used a strip of plastic with a strip of absorbent paper adhered along one side of the plastic and a wire electrode extending through the strip of absorbent paper. The wire electrode and the strip of absorbent paper had a length to encircle the limb of the infant and, in use, the wire electrode was bent to conform around the limb. This limb band did not have an adhesive for attaching the band to the skin and, in use, required the addition of a saline solution to the absorbent paper to provide and maintain conductivity between the wire electrode and the skin.

A band that encircles the limb of a patient must be applied sufficiently loosely to avoid interference with circulation. Limb band electrodes of the type that are adapted to form an electrical contact with the skin around the entire periphery of the limb, can produce artifacts due to muscular contractions and changes in pressure and contact area between the band and the skin of the subject.

Biomedical electrodes have also heretofore been made in which an electrode pad having an electrically conductive electrode member was adapted to be adhesively secured by a pressure sensitive solid gel adhesive to a localized area of the infant's body. However, an electrode mounted on a patient's limb, is subjected to limb movement and the electrode lead wire exerts forces on the connection of the lead wire to the electrode pad and on the adhesive attachment of the electrode pad to the skin. The skin composition of premature infants and particularly gram weight neonatals is very thin and delicate and it is important to minimize stressing or irritating of the infant's skin and prevent potential infection or additional trauma.

SUMMARY OF THE INVENTION

It is an object of the present invention to provide an improved biomedical electrode for use on the limb of a patient and which reduces electrical artifacts and stressing of the skin during limb movement.

Accordingly, the present invention provides a composite electrode pad of the type adapted for connection by a lead wire to an external sensing or monitoring apparatus and having an electrically conductive solid gel adhesive for adhesively securing the electrode pad to a localized area of a limb, and a composite limb band having one end attached to the electrode pad and adapted to encircle the limb and be retracted upon itself to function as a strain relief for the lead wire. The composite limb band includes an elongated conformable first band of non-woven spunlaced fibers such as dimensionally stable second band of non-woven spunbonded filaments adhesively secured to an inner face of the first band along an intermediate portion of the latter. The inner face of one end portion of the first band is adhesively secured to the outer side of the electrode pad and a pressure sensitive adhesive is provided on the inner face of a second end portion of the first band for adhesively attaching the second end portion of the first band to the outer side of the first band adjacent the first end portion.

The end portions of the composite limb band have the soft conformable characteristics provided by the non-woven spunlaced first band, and the dimensionally stable second band of non-woven spunbonded filaments gives the intermediate portion of the composite limb band strength and stretch resistance. The non-woven spunlaced first band and the non-woven spunbonded second band are porous and the composite limb band is breathable and does not trap moisture next to the skin. The spunlaced first band is preferably apertured to enhance breathability of the limb band and the first and second bands are preferably formed of polyester fiber so that the limb band does not absorb moisture but instead allows it to wick away from the skin and evaporate.

BRIEF DESCRIPTION OF THE DRAWINGS

FIG. 4 is an exploded longitudinal sectional view (not to scale) of the biomedical electrode and limb band illustrating parts on a scale larger than full size;

FIG. 5 is a longitudinal sectional view (not to scale) through the assembled biomedical electrode and limb band; and FIG. 6 is a longitudinal sectional view through a modified form of biomedical electrode with limb band.

DETAILED DESCRIPTION

Figure 1:
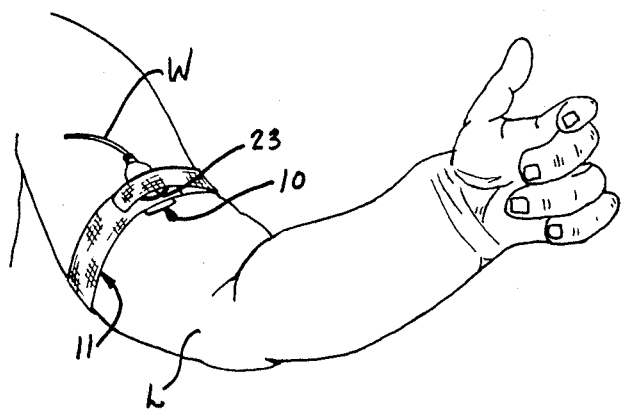
FIG. 1 is a perspective view of the biomedical electrode with limb band of the present invention shown applied to a limb of an infant.

The disposable biomedical electrode of the present invention is adapted for use on the limb of a subject and particularly on the limbs of infants and neonatals. In general, the biomedical electrode includes a composite electrode pad designated generally by the numeral 10 adapted to be adhesively secured to a localized area on the limb, and a composite limb band 11 adapted to encircle a limb designated L in FIG. 1, such as an upper arm or leg of a patient.

The composite electrode pad 10 includes an electrically conductive electrode member 15 having a layer 17 of electrically conductive solid gel adhesive electrically contacting one side of the conductive member and providing a skin contacting adhesive surface at the lower side of the electrode pad. The electrically conductive manner 15 is preferably of the type which includes a plate portion 15a having a lower surface in contact with the layer of solid gel adhesive 17, and a connector head 15b at its upper side for connecting the conductive member to an external monitoring or sensing apparatus. As is well known in the art, the conductive member 15 can be formed of a conductive metal such as silver or silver plated plastic such as ABS, with a silver-silver chloride coating on the lower surface. A backing sheet 18 of conformable non-conductive material overlies the upper surface of the plate portion 15a and has an opening therethrough for receiving the connector head 15b. The lower surface of the backing sheet 18 is preferably coated with a thin porous layer of a hypoallergenic adhesive such as acrylic medical grade pressure sensitive adhesive indicated by the heavy line 16 and the lower side of the backing sheet is adhesively secured to the upper side of the plate portion 15a. The backing sheet extends outwardly from the periphery of the plate portion and the layer of adhesive gel 17 is in adhering contact with the outer peripheral portion of the backing sheet and is preferably coextensive therewith. A release sheet 21 of plastic or plastic coated paper is provided at the under side of the layer of adhesive gel 17 to protect the adhesive prior to application of the electrode to the skin of a patient.

In the preferred embodiment shown in FIGS. 1-5, the conductive member is adapted for connection by a detachable snap or clip-on connector to a lead line leading to the sensing or monitoring apparatus. As shown, an electrically conductive cap 22, formed of either a conductive metal or a non-conductive material which is plated to be conductive, is mounted on the electrode attaching head 15b in electrically conductive relation therewith. The cap 22 is adapted for detachable electrical connection to a conventional snap-on or clip-on connector 23 on a lead wire W as shown in FIG. 1.

When the electrodes are mounted on the limb of a patient, there is frequent relative motion between the limb and the lead wire and the composite limb band 11 is provided and arranged to encircle the limb and be reattached upon itself to reduce the transmission of forces from the lead wire W to the connection of the lead wire to the electrode pad, and also reduce the transmission of forces from the pad to the skin of the patient. The composite limb band 11 includes a first elongated band 25 of non-woven spunlaced fabric having a length sufficient to encircle the limb of a patient and have the end portions overlap, and an elongated, dimensionally stable second band 26 of non-woven spunbonded fabric. The first band 25 of non-woven spunlaced fabric has a thin porous adhesive coating such as an acrylic medical grade pressure sensitive adhesive indicated by the heavy line 27, extending along the under side and coextensive therewith. One end portion 25a of the first band is secured by the adhesive coating to the upper side of the electrode pad 10 and the end portion 25a has an opening 30 therethrough registering with the cap 22. The second band 26 of non-woven spunbonded fabric is secured by the adhesive layer 27 to an intermediate portion 25b of the first band to give strength and inhibit stretching of the intermediate portion. The second band 26 is shorter than the first band and a second end portion 25c of the first band extends beyond the end of the second band. The pressure sensitive adhesive coating 27 on the second end portion 25c of the first band is adapted to adhesively attach the second end portion of the first band in overlapping relation to the first end portion and to the electrical connector 23 when the electrode pad 10 and limb band 11 are applied to the limb of the patient as shown in FIG. 1. A release liner sheet 28 of plastic or plastic coated paper is applied to the adhesive coating 27 on the end portion 25c, to protect the adhesive coating prior to application of the limb band to the limb of a patient.

As used herein, the phrase "non-woven spunlaced fabric" means a non-woven web of fibers that are mechanically interlaced and entangled without chemical or thermal bonding of the fibers. The phrase "non-woven spunbonded fabric" means a non-woven web of relatively crossing filaments that are bonded together at the filament junctions. The end portions of the composite limb band have the soft conformable characteristics provided by the non-woven spunlaced fabric of the first band and the dimensionally stable second band of non-woven spunbonded fabric gives the intermediate portion of the composite limb band strength and stretch resistance. Thus, the end portion 25a of the first band can readily conform to the contour of the upper surface of the composite electrode pad and the second end portion 25c can conform to the contours of the first end portion and to the electrode pad and lead wire connected thereto, when the second end portion is overlapped and secured by the adhesive thereon to the outer face of the first band. The first band 25 is preferably formed of 100% polyester fibers and the second band 26 is also preferably formed of 100% polyester filaments that are bonded at the filament junctions without added binder or adhesive. The polyester fibers are non-allergenic and do not absorb moisture and the first and second bands are porous so that the composite band is breathable and allows moisture to evaporate. The spunlaced first band is preferably of an apertured type as illustrated in the encircled portion in FIG. 2, to enhance porosity and breathability, particularly in the end portions that overlie the electrode pad. A presently preferred fabric for forming the first band is a non-woven spunlaced fabric of 100% polyester marketed by E. I. duPont deNemours and Company under the trademark "Sontara" ®, Style No. 8021. This non-woven spunlaced material is an apertured type fabric and has a unit weight of about 2.1 to 2.7 ounces per square yard and a thickness of about 0.024 to 0.030 inches (ASTM test method D1117 Sec. 19). A presently preferred material for forming the second band is a non-woven 100% polyester marketed by E. I. duPont deNemours and Company under the trademark "Reemay" ®, Style No. 2250. This non-woven spunbonded material is formed of low denier 100% polyester filaments that randomly cross and which are bonded at the filament intersections by heat and pressure without added binders or adhesives, as illustrated in the encircled portion in FIG. 3 and the material has a nominal basis weight of about 0.5 to 0.7 ounces per square yard and a thickness of about 0.005 to 0.006 inches. A presently preferred skin compatible electrically conductive pressure sensitive solid gel adhesive for layer 17 is marketed by Medtronic, Inc. under the tradename "Promeon" No. RG63b. FIGS. 3 through 6 are not to scale and the thickness of the bands 25, 26 and adhesive layer 17 are shown somewhat greater than actual size, to facilitate illustration.

A modified form of electrode pad and limb band is shown in FIG. 6 and like numerals are used to designate the same parts and like numerals followed by the postscript ' are used to designate modified parts. In this embodiment, the connector head 15b' on the electrically conductive member 15' is permanently attached to a lead wire W' as by crimping or welding on an electrically conductive adhesive, and the first end portion 25a' of the first band 25' overlies and is adhered to the connector head 15b' and the lead wire 24'. The construction and materials used is otherwise the same as that illustrated and described in connection with FIGS. 1-5.

Figure 2:
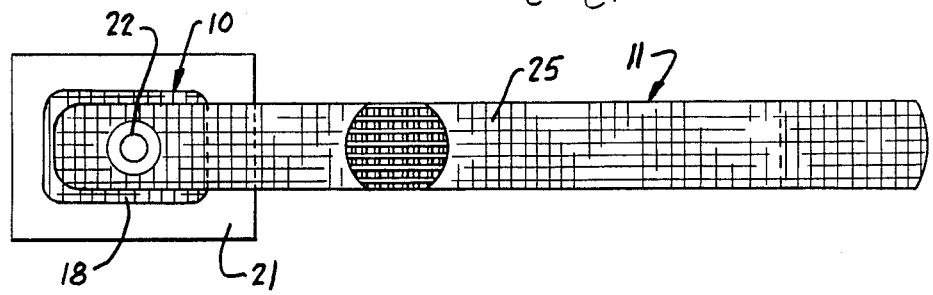
FIG. 2 is a top view of the biomedical electrode and limb band with an encircled portion of the upper side of the limb band shown on a larger scale to facilitate illustration.
Figure 3:
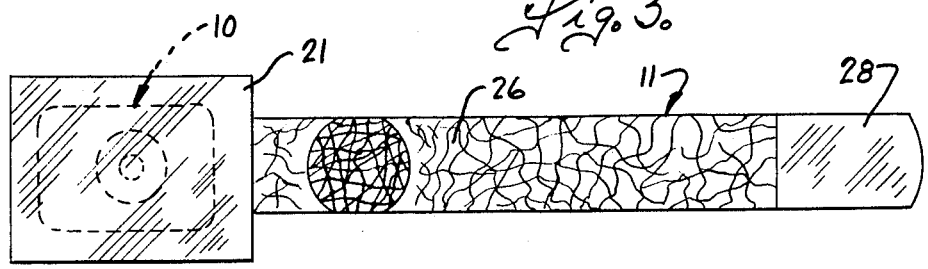
FIG. 3 is a bottom view of the biomedical electrode and limb band with an encircled portion of the lower side of the limb band shown on a larger scale to facilitate illustration.

The biomedical electrode with limb band is particularly adapted for use in sensing and monitoring premature and neonatal infants and the electrode pad and limb band for use on such infants is shown approximately full size in FIGS. 2 and 3. A composite limb band having an overall length of about five inches is sufficient to encircle the limb of neonatal infants and allow the end portions to overlap. The composite band, when applied functions to reduce transmission of stresses from the lead wire to the connecton of the lead wire to the electrode pad and to the adhesive interface between the electrode pad and the skin of the infant. It has been found that electrode pads having only a relative small skin contact area, for example of the order of ½ to ¾ square inches, can be used with the limb band. As shown in FIGS. 2 and 3, the electrode pad has a generally rectangular face a width of about ¾ inches and a length of about ⅞ inches. The limb band does not adhere to the skin of the patient and does not cause irritation or impede evaporation of moisture from the skin.

The embodiments of the invention in which an exclusive property or privilege is claimed or defined as follows:

1. A biomedical electrode for use on a limb of a patient comprising, a composite electrode pad having upper and lower sides, the composite electrode pad including an electrically conductive member having means for connection to an external apparatus, and a layer of electrically conductive solid gel adhesive electrically contacting the conductive member and providing a skin contacting adhesive surface at the lower side of the electrode pad, a limb band including an elongated conformable first band of non-woven spunlaced fabric having inner and outer sides, the first band including first and second end portions and an elongated intermediate portion and a length sufficient to encircle a limb of a patient and have the second end portion overlap the first end portion, adhesive means securing the inner side of the first end portion of the first band to the upper side of the electrode pad, an elongated dimensionally stable second band of non-woven spunbonded fabric, adhesive means securing one side of the second band to the inner side of the first band along the intermediate portion of the latter to inhibit stretching of the intermediate portion of the first band during use, and pressure sensitive adhesive means on the inner side of the second end portion of the first band for attaching the second end portion to the outer side of the first band adjacent the first end portion.

2. A biomedical electrode according to claim 1 wherein said first band consists of polyester fibers.

3. A biomedical electrode according to claim 1 wherein the second band consists of polyester filaments randomly crossing and self bonded at the filament junctions without added binder or adhesive.

4. A biomedical electrode according to claim 1 wherein said first band is apertured to enhance breathability.

5. A biomedical electrode according to claim 1 wherein said first and second bands are each formed of 100% polyester and said first band is apertured to enhance breathability.

6. A biomedical electrode according to claim 1 wherein said conductive member includes a plate portion and a post integral with said plate portion, said means for connection to an external apparatus including a lead wire having one end fixedly connected to said post, said first end portion of the first band overlying said post and said one end of the lead wire.

7. A biomedical electrode according to claim 1 wherein said conductive member includes a plate portion and an electrical connector head extending from the plate portion and adapted to detachably receive a mating electrical connector, said first end portion of the first band having an opening therethrough registering with the electrical connector head.

8. A biomedical electrode for use on a limb of a subject comprising, an electrode member including a plate portion having upper and lower surfaces and electrode attaching means on the upper surface of the plate portion, a backing sheet of conformable non-conductive material having a lower side and an upper side and an opening therethrough receiving the electrode attaching means, the backing sheet being larger than the plate portion and having an outer portion extending outwardly of the periphery of the plate portion, a layer of biomedical electrically conductive pressure sensitive adhesive gel on the lower surface of the plate portion and on the lower side of the outer portion of the backing sheet, an elongated conformable first band of non-woven spunlaced polyester fibers, the first band having an elongated intermediate portion and first and second end portions and a length sufficient to encircle a limb of a subject with the second end portion overlapping the first end portion, the first band having inner and outer sides, adhesive means securing the inner side of the first end portion of the first band to the upper side of the backing sheet, an elongated dimensionally stable second band of non-woven randomly crossing spunbonded polyester filaments self-bonded at the filament junctions, adhesive means securing one side of the second band to the inner side of the first band along the intermediate portion of the latter to inhibit stretching of the intermediate portion of the first band during use, and pressure sensitive means on the inner side of the second end portion of the second band for attaching the second end portion of the first band to the outer side of the first band adjacent the first end portion.

9. A biomedical electrode according to claim 8 wherein said second band has a thickness substantially less than the thickness of the first band.

10. A biomedical electrode according to claim 8 wherein said first band is apertured to enhance breathability.

11. A biomedical electrode according to claim 8 wherein said electrode attaching means includes a post integral with said plate portion of the electrode member and a lead wire having one end fixedly connected to said post, said first end portion of the first band overlying said post and said one end of the lead wire.

12. A biomedical electrode according to claim 8 wherein said electrode attaching means includes an electrical connector head extending from the upper surface of the plate portion of electrode member and adapted to detachably receive a mating electrical connector, said first end portion of the first band having an opening therethrough registering with the electrical connector head.

* * * * *